United States Patent [19]

Ahrens et al.

[11] Patent Number: 5,036,696
[45] Date of Patent: Aug. 6, 1991

[54] METHOD FOR MEASURING FRACTURE TOUGHNESS OF BRITTLE MEDIA

[75] Inventors: Thomas J. Ahrens, Pasadena, Calif.; Allan M. Rubin, Providence, R.I.

[73] Assignee: The United States of America as represented by the Secretary of the Air Force, Washington, D.C.

[21] Appl. No.: 561,406

[22] Filed: Jul. 30, 1990

[51] Int. Cl.⁵ .............................................. G01N 3/08
[52] U.S. Cl. .......................................... 73/12; 73/799
[58] Field of Search ................... 73/12, 799, 834, 821, 73/598, 597

[56] References Cited

U.S. PATENT DOCUMENTS

| | | |
|---|---|---|
| 4,210,028 | 7/1980 | Hildebrand . |
| 4,413,517 | 11/1983 | Soden . |
| 4,418,563 | 12/1983 | Kalthoff et al. .......................... 73/12 |
| 4,522,071 | 1/1985 | Thompson . |
| 4,602,511 | 7/1986 | Holt . |

OTHER PUBLICATIONS

"The Effect of Oriented Cracks on Seismic Velocities", D. L. Anderson et al, J. Geophys Res. 79:26, 4011-26 (Sep. 10, 1974).
"Seismic Velocities in Dry and Saturated Cracked Solids", by R. J. O'Connell, J. Geophys Res. 79:35, 5412-26 (Dec. 10, 1974).
"Dynamic Tensile Strength of Lunar Rock Types", by S. N. Cohn et al., J. Geophys Res., 86:B3, 1794-1802 (Mar. 10, 1981).
"Dynamic Rock Fragmentation", by Grady et al, Chap. 10, in *Fracture Mechanics of Rock*, Atkinson, et al, Academic Press (1987).
"Experimental Fracture Mechanics Data for Rocks and Minerals", by Atkinson et al, Chap. 11, in *Fracture Mechanics of Rocks*, Atkinson ed, Academic Press (1987).

*Primary Examiner*—Robert Raevis
*Attorney, Agent, or Firm*—Bobby D. Scearce; Donald J. Singer

[57] ABSTRACT

A method for measuring fracture toughness of a brittle material is described which comprises the steps of impacting a sample of the material of preselected thickness and predetermined density and characteristic ultrasonic wave velocity $C_i$ at preselected velocity with a projectile of material having a known density and characteristic shock impedence corresponding to a predetermined characteristic ultrasonic wave velocity, determining the stress $\sigma$ at which the sample fractures upon impact of the projectile, and determining the fracture toughness of the sample as equal to $2\sigma(c_i t/\pi)^{\frac{1}{2}}$, where t is the calculated time duration of a tensile pulse traveling the thickness of the sample.

4 Claims, 2 Drawing Sheets

METHOD FOR MEASURING FRACTURE TOUGHNESS OF BRITTLE MEDIA

RIGHTS OF THE GOVERNMENT

The invention described herein may be manufactured and used by or for the Government of the United States for all governmental purposes without the payment of any royalty.

BACKGROUND OF THE INVENTION

The present invention relates generally to materials testing methods, and more particularly to a method for measuring fracture toughness of brittle media.

The invention defines a sensitive method using onset of sound velocity reduction in measuring fracture toughness of a material. A projectile is accelerated against a sample of the material and measured ultrasonic wave velocities in the sample are used to determine fracture toughness. Velocity measurements at various stress levels and impact durations provided consistent values for fracture toughness.

It is therefore a principal object of the invention to provide a method for measuring fracture toughness of brittle media.

It is a further object of the invention to provide a method for measuring fracture toughness of materials utilizing measurement of ultrasonic velocities in the material.

These and other objects of the invention will become apparent as a detailed description of representative embodiments proceeds.

SUMMARY OF THE INVENTION

In accordance with the foregoing principles and objects of the invention, a method for measuring fracture toughness of a brittle material is described which comprises the steps of impacting a sample of the material of preselected thickness and predetermined density and characteristic ultrasonic wave velocity $c_i$ at preselected velocity with a projectile of material having a known density and characteristic shock impedance corresponding to a predetermined characteristic ultrasonic wave velocity, determining the stress $\sigma$ at which the sample fractures upon impact of the projectile, and determining the fracture toughness of the sample as equal to $2\sigma(c_i t/\pi)^{\frac{1}{2}}$, where t is the calculated time duration of a tensile pulse traveling the thickness of the sample.

DESCRIPTION OF THE DRAWINGS

The invention will be more clearly understood from the following detailed description of representative embodiments thereof read in conjunction with the accompanying drawings wherein.

DETAILED DESCRIPTION

Figures 1, 2:
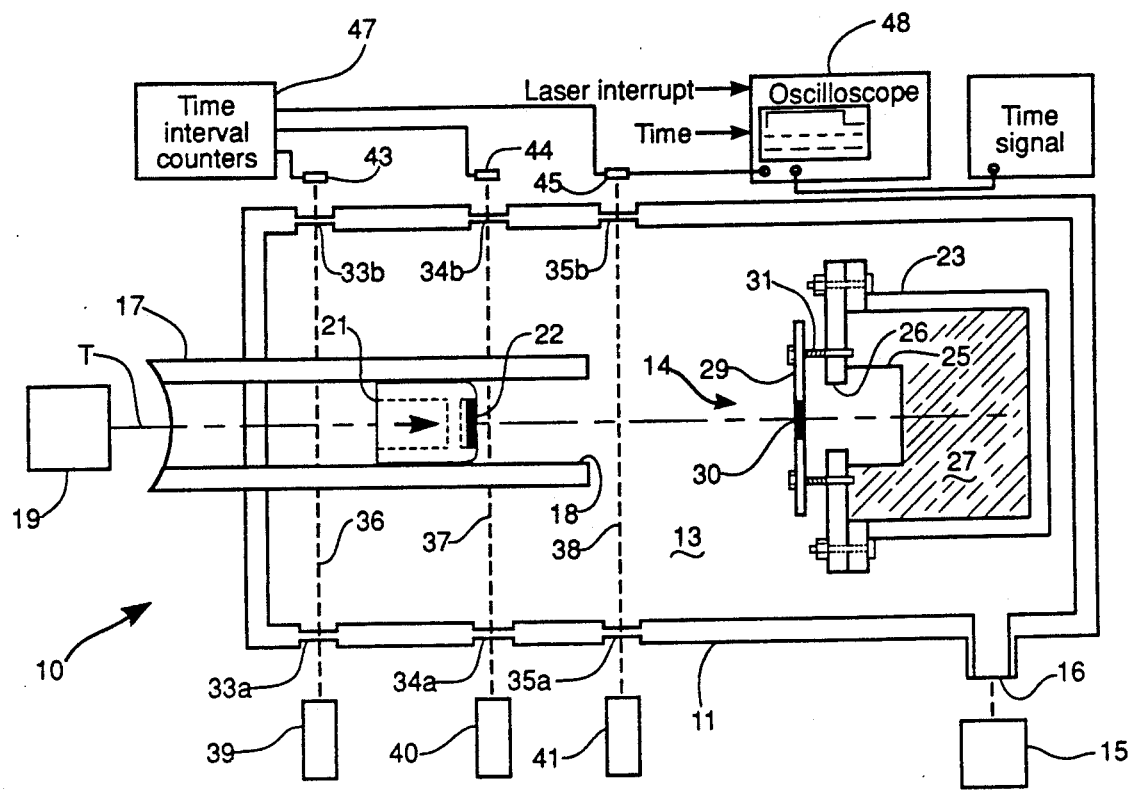
FIG. 1 is a schematic plan view of a representative system for performing the method of the invention.
FIG. 2 is a sequence chart of 11 stages of shock wave development at impact using the FIG. 1 system in performing measurements of fracture toughness of Bedford limestone.

Referring now to the drawings, FIG. 1 shows a schematic plan view of a representative system 10 comprising housing 11 defining chamber 13 including test region 14 wherein samples are impacted in practicing the method of the invention. Vacuum pump 15 is operatively connected to vacuum port 16 for selectively evacuating chamber 13. Gas gun 17 defining muzzle 18 is operatively connected to compressed gas source 19 (such as compressed air) providing means for selectively propelling test projectile 21 along axis T. Projectile 21 may comprise any suitable material such as Lexan TM or polymethylmethacrylate (PMMA), and may have attached to the forward end thereof an impact (flyer) plate 22 of aluminum, PMMA, Lexan TM or other material having characteristic low shock impedence and appropriate mechanical strength for impacting brittle sample materials. Plate 22 is circumferentially supported in the end of projectile 21 so that the front and rear faces of plate 22 are unsupported free surfaces. Recovery tank 23 is disposed inside housing 11 along axis T as suggested in FIG. 1, defines target trap 25 adjacent opening 26 and includes shock absorbent recovery medium 27 such as loose cloth rags surrounded by foam rubber. Sample holder 29 is mounted on recovery tank 23 for supporting sample 30 along axis T. Alignment fixture 31 allows selective alignment of sample 30 with respect to axis T.

Sets of optical windows $33a,b, 34a,b, 35a,b$ are defined in the walls of housing 11 for projecting laser beams 36,37,38 from laser sources 39,40,41 across chamber 13 and gun 17. Laser beams 36,37,38 are used in velocity measurements on projectile 21. Disposed near windows $33b, 34b, 35b$ are laser detectors 43,44,45 connected to time interval counter 47 and auxiliary electronics 48 for measuring the time duration of any interruption of laser beams 36,37,38 by projectile 21 propelled along axis T. With the spacing between projection axes of laser beams 36,37,38 known, projectile 21 velocity can be determined both by travel time between two of the beams and by the duration of interruption of the third beam by projectile 21. Projectile 21 velocity may be determined by means other than that just described as would occur to one skilled in the field of the invention guided by these teachings, the velocity measuring means not being considered limiting of these teachings or of the appended claims.

In tests performed in demonstration of the invention, samples 30 of Bedford limestone (density 2.62 g/cc) were impacted with a Lexan TM projectile carrying an aluminum or PMMA plate 22 accelerated by a 40 mm compressed air gun 17 at controlled velocities of 10–30 m/s. Samples 30 were approximately 2.5 cm diameter by 0.75 cm thick with the front and rear faces polished flat and parallel within 0.005 mm. In the test setup, front and rear faces of samples 30 were aligned perpendicularly of axis T to ensure planar impact between plate 22 and samples 30. At impact, sample 30 breaks from support 29 and is propelled into target trap 25 where it is protected from further damage by absorbent recovery medium 27.

FIG. 2 is a diagram of a sequence of 11 stress states produced at impact of projectile 21 with samples 30 of Bedford limestone. The listing along the right side of FIG. 2 represents approximate time intervals for events occurring in the fracture process for sample 30. The specific sequence and timing may vary substantially with sample 30 material type, wave velocity, and sample 30 and plate 22 thicknesses. Stress level is a function of material impedances and impact velocity. Upon impact, initial compression waves 50 propagate away from impact plane 51 between projectile 21 and sample 30, are reflected from the rear surface of plate 22 front and rear surface of sample 30, and are superimposed in the middle of sample 30 which results in uniaxial extension with about 1 μs duration. Tension is produced within sample 30 when reflections of compressive waves 50 meet within sample 30, as at location 57, at which point the onset of fracture occurs.

The magnitude of compressive stress $\sigma_t$ within sample 30 is derived from equations of conservation of mass and momentum across the shock front which provide, $$\sigma_t = \frac{\rho_i c_i \rho_t c_t}{\rho_i c_i + \rho_t c_t} U_i \quad (1)$$

where $\rho$ is density, c is shock wave velocity, subscripts i and t refer to plate 22 and sample 30, respectively, and $U_i$ is projectile 21 impact velocity (see Cohn et al, J Geophys Res 86, 1794-1802 (1981) the teachings of which are incorporated herein by reference). In equating $\sigma_t$ with the resulting tensile stress at location 57 following reflection and superposition of stress waves, it may be assumed to an acceptable approximation that wave 50 velocities at the moderately low stresses encountered (up to 100 MPa) are equal to the corresponding ultrasonic velocities; that because of the greater strength of rock in compression than tension, no damage or wave attenuation occurs during the initial compressive pulse; and that the velocity of the reflected tensile pulse (rarefaction wave) is the same as that of the incident compressive wave, which allows the stress pulse durations to be computed from the material ultrasonic longitudinal wave velocity. In the example of FIG. 2, plate 22 thickness (PMMA) is chosen so that the reflected tensile pulses meet at the center of sample 30; tension is first introduced when the stress wave has traversed 1.5 times sample 30 thickness, and ends (if spalling does not occur) when the stress wave has traversed 2.5 times sample 30 thickness. If plate 22 is thinner or comprises material having an impedence corresponding to a large characteristic longitudinal sonic wave velocity (e.g., aluminum), then tension is first introduced at a location between the rear surface and the center of sample 30 and is of shorter duration, viz., the time required for the stress wave to traverse twice the flyer plate thickness (equivalent to the situation in FIG. 2 but with the rear surface of sample 30 displaced further from the impact plane). Plate 22 thickness is therefore selected at about 0.16 to 0.20 cm for PMMA and 0.14 to 0.18 cm for aluminum depending on sample 30 material and thickness. It may also be assumed that the tests are one-dimensional, that is, sample 30 edges are sufficiently far from the center that information has not propagated from the edges to the center of sample 30 prior to cessation of tension. For measurements taken in demonstration of the invention, a sample 30 diameter-to-thickness ratio of 3.3 or greater was sufficient. The smaller ratio results in suppression of radial cracking of sample 30. Finally, it may be assumed that the magnitude of the reflected tensile pulse is that of the compressive pulse impacting the rear surface of sample 30.

Figure 3A:
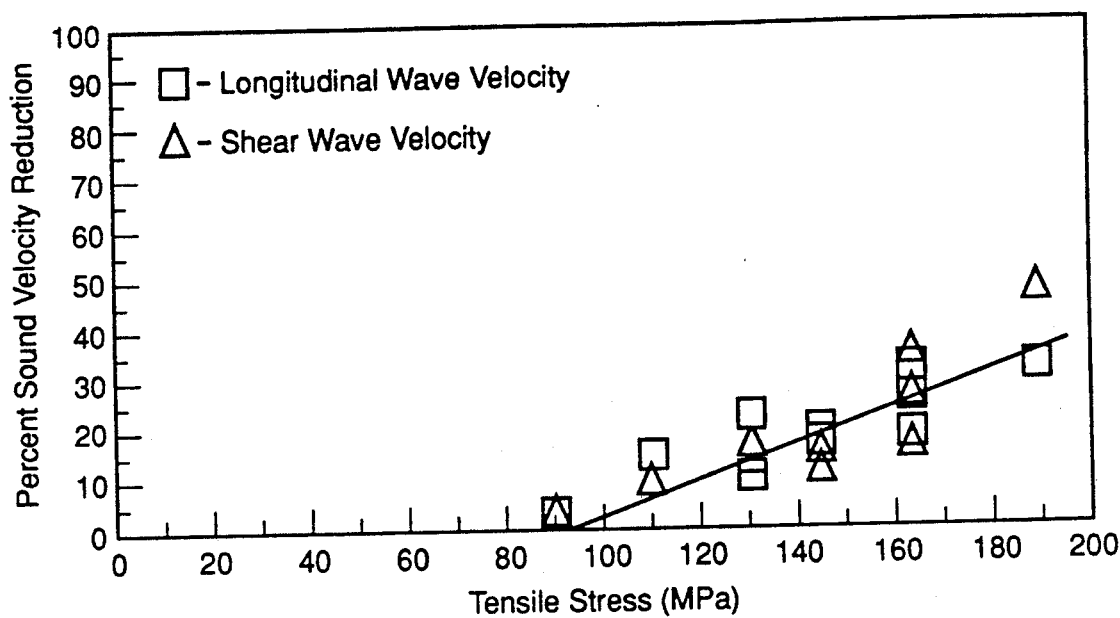
FIGS. 3a and 3b show respective graphs of percent sound velocity reduction versus tensile stress in Bedford limestone samples.
Figure 3B:
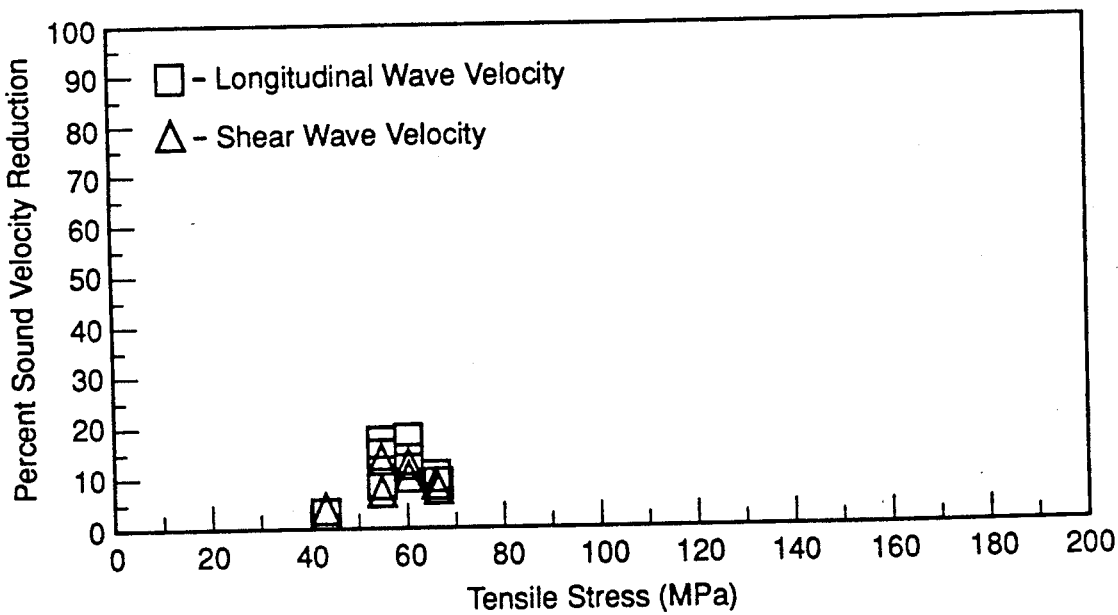

FIGS. 3a and 3b show respective graphs of percent sound velocity reduction versus tensile stress in impacted Bedford limestone specimens using an aluminum impact plate 22 (FIG. 3a) and a PMMA impact plate 22 (FIG. 3b) to determine onset of dynamic tensile failure. Both longitudinal wave and shear wave velocities were measured In accordance with a governing principle of the invention, onset of tensile failure is determinative of fracture toughness of rock. Results shown in FIGS. 3a,3b show that tensile failure occurs at computed stresses of about 180 MPa for the shorter duration (0.5 μs) aluminum plate tests, and about 70 MPa for the longer duration (1.2 μs) PMMA plate tests. In the shorter duration tests, velocity reductions increase nearly linearly over a wide range of peak stresses less than the ultimate tensile strength, whereas in the longer duration tests, velocity reductions at stresses less than the ultimate tensile strength occur over a much narrower interval, are less consistent and lower in magnitude. Percent reduction in longitudinal and shear wave velocities are substantially equal.

Tensile strengths measured at high strain rates can be considerably higher than those measured quasi-statically (Rinehart, Proc 7th Sym on Rock Mech, 1, 205-208 (1965). This result can be modelled in terms of fracture mechanics theory (Grady et al, "Dynamic Rock Fragmentation, in *Fracture Mechanics of Rock*, Atkinson, Ed, Academic Press, London (1987)). During quasi-static tests, assuming sufficient pre-existing microcracks that all orientations are represented, sample failure occurs when the stress $\sigma$ is increased to the point that the largest crack can extend, at which point the crack stress intensity factor K equals the fracture toughness $K_c$ of the material. For a circular crack, $$K = 2\sigma(a/\pi)^{\frac{1}{2}}. \quad (2)$$

where a is the crack half-length. Under dynamic loading, the criterion for crack propagation ($K = K_c$) remains the same, but for a suddenly applied load for early time $t < a/c_s$, K increases with t as, $$K \approx 2\sigma(c_s t/\pi)^{\frac{1}{2}} \quad (3)$$

where $c_s$ is the shear-wave velocity (the effective crack length $c_s t$ increases with time). Thus a suddenly applied load can exceed the static strength of the material for $c_s t < a$ without producing failure. The greater the suddenly applied stress, the sooner $\sigma(c_s t)^{\frac{1}{2}} = K_c$, and the sooner fracture will initiate.

If the stresses in the dynamic tests are greater than the static strength of the material, so that $c_s t < a$, for a equal to the largest inherent flaw size, Eq (3) can be used to compute the fracture toughness from the test data. In these short duration tests, failure will occur at stresses for which K in Eq (3) exceeds $K_c$, where t is the duration of the tensile stress pulse. The shear wave velocity of intact Bedford limestone was determined to be 2.8 km/s. Assuming that onset of crack extension produces a measurable reduction in sample sound velocity, then crack extension first occurs at a stress of approximately 90 MPa for the 0.5 μs pulse and 50 MPa for the 1.2 μs pulse. Eq (3) then yields:

$K_c(1.2 \mu s) = 3.3 \text{ MPam}^{\frac{1}{2}}$ (PMMA plate material)

$K_c(0.5 \mu s) = 3.8 \text{ MPam}^{\frac{1}{2}}$ (aluminum plate material)

Thus the demonstration tests provided a consistent value of $3.6 \pm 0.3$ MPam$^{\frac{1}{2}}$ for fracture toughness, which results are somewhat higher than that previously reported (see e.g., Atkinson et al, "Experimental Fracture Mechanics Data for Rocks and Minerals", in *Fracture*

*Mechanics of Rocks,* Atkinson, Ed, Academic Press, London (1987)).

At stresses higher than those producing the first cracking, cracking is initiated sooner ($\sigma$ is larger so t is smaller in Eq (3)), so cracks have more time to grow, and smaller cracks are activated, so presumably the activated flaws are closely spaced. Complete tensile failure occurs at an applied stress sufficiently high that the density of activated cracks is sufficient for them to coalesce in the short duration of stress application. Tensile strengths were about 70 MPa for the 1.2 $\mu$s tests and 180 MPa for the 0.5 $\mu$s tests. Using fracture toughness values of 3.3 and 3.8 MPam$^{\frac{1}{2}}$, this implies that cracks with half-lengths greater than 1.7 mm were activated after 0.62 $\mu$s in the 1.2 $\mu$s tests, and that cracks with half-lengths greater than 0.35 mm were activated after 0.12 $\mu$s in the 0.5 $\mu$s tests. Once crack growth is initiated, propagation velocities are about one-third the longitudinal sound velocity in the solid, determined to be 4.8 km/s for Bedford limestone. Thus cracks may extend by about 1.0 mm in each direction from the 3.4 mm starter cracks in the remaining 0.6 $\mu$s of the 1.2 $\mu$s tests, and 0.6 mm from the 0.7 mm starter cracks in the remaining 0.38 $\mu$s of the 0.5 $\mu$s tests.

The invention therefore provides a method for measuring fracture toughness of brittle media. It is understood that modifications to the invention may be made as might occur to one skilled in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. A method for measuring fracture toughness of brittle material, comprising the steps of:
  (a) providing a sample of said brittle material, said sample having preselected thickness and predetermined density and characteristic ultrasonic shear wave velocity $c_s$;
  (b) impacting said sample with a projectile at preselected velocity, said projectile including an impactor plate comprising material having a known density and characteristic shock impedance corresponding to a predetermined characteristic ultrasonic wave velocity;
  (c) determining the stress $\sigma$ within said sample at which fracture of said sample occurs upon impacting said sample with said projectile and impactor plate; and
  (d) determining the fracture toughness of said sample as equal to $2\sigma(c_s t/\pi)^{\frac{1}{2}}$, where t is the calculated time duration of a tensile pulse traveling the thickness of said sample and is given by $2D/c_i$, where D is the thickness and $c_i$ is the ultrasonic compression wave velocity of said impactor plate.

2. A method for measuring fracture toughness of brittle material, comprising the steps of:
  (a) providing a sample of said brittle material, said sample having preselected thickness and predetermined density $\rho_t$ and characteristic ultrasonic shear wave velocity $c_s$;
  (b) impacting said sample with a projectile at preselected velocity U, said projectile including an impactor plate comprising material having a known density $\rho_i$ and characteristic shock impedance corresponding to a predetermined characteristic ultrasonic wave velocity $c_i$;
  (c) determining the stress $\sigma$ within said sample at which fracture of said sample occurs upon impacting said sample with said projectile, according to the relationship:

$$\sigma = \frac{\rho_i c_i \rho_t c_t}{\rho_i c_i + \rho_t c_t} U$$

and
  (d) determining the fracture toughness of said sample as equal to $2\sigma(c_s t/\pi)^{\frac{1}{2}}$, where t is the calculated time duration of a tensile pulse traveling the thickness of said sample and is given by $2D/c_i$, where D is the thickness and $c_i$ is the ultrasonic compression wave velocity of said impactor plate.

3. The method of claim 2 wherein said projectile material is selected from the group consisting of polymethylmethacrylate, aluminum and Lexan ™.

4. The method of claim 2 wherein said sample is impacted at an impact velocity of 10 to 30 meters per second.

* * * * *

UNITED STATES PATENT AND TRADEMARK OFFICE
CERTIFICATE OF CORRECTION

PATENT NO. : 5,036,696

DATED : August 6, 1991

INVENTOR(S) : Thomas J. Ahrens et al

It is certified that error appears in the above-identified patent and that said Letters Patent is hereby corrected as shown below:

Column 3, line 4, -- 55 -- should follow "surface".
Column 4, line 1, a period should follow "measured".
Column 6, line 18, "$c_s$" should be -- $c_t$ --.
Column 6, line 35, "$c_s t$" should be -- $c_t t$ --.

Signed and Sealed this

Second Day of March, 1993

Attest:

STEPHEN G. KUNIN

*Attesting Officer*     *Acting Commissioner of Patents and Trademarks*